United States Patent [19]

Green

[11] 4,021,459
[45] May 3, 1977

[54] PROCESS FOR THE PREPARATION OF 21-HALOGENO-21-DESOXY-17α-ACYLOXY 20-KETO-PREGNENES

[75] Inventor: Michael J. Green, East Brunswick, N.J.

[73] Assignee: Schering Corporation, Kenilworth, N.J.

[22] Filed: Aug. 14, 1975

[21] Appl. No.: 604,673

[52] U.S. Cl. .................. 260/397.45; 260/239.55 D
[51] Int. Cl.² ......................................... C07J 5/00
[58] Field of Search .............. 260/397.45, 239.55 D

[56] References Cited
UNITED STATES PATENTS 3,832,366   8/1974   Cimarusti ..................... 260/397.45

Primary Examiner—Elbert L. Roberts
Attorney, Agent, or Firm—Mary S. King; Stephen B. Coan; Bruce M. Eisen

[57] ABSTRACT

21-Halogeno-17α-acyloxy-20-keto-4-pregnenes having physiological properties are prepared by the reaction of a 17α,21-dihydroxy-20-keto-4-pregnene 17α,21-orthoester with a triphenylmethyl halide in an organic solvent, said halide being chloride or bromide.

9 Claims, No Drawings

PROCESS FOR THE PREPARATION OF 21-HALOGENO-21-DESOXY-17α-ACYLOXY 20-KETO-PREGNENES

FIELD OF INVENTION

This invention relates to a novel process for the manufacture of 21-halogeno-17α-acyloxy-20-ketopregnenes.

More specifically, this invention relates to a process for preparing 21-chloro- and 21-bromo-17α-hydrocarbonylcarbonyloxy-20-keto-4-pregnenes which are known, physiologically active steroids.

PRIOR ART

Known in the art are 21-chloro- and 21-bromo-17α-acyloxy-20-keto-4-pregnenes and the 1-dehydro-, 6-dehydro- and 1,6-bis-dehydro analogs thereof which possess progestational, glucocorticoid and anti-inflammatory activities.

The prior art methods for preparing the 21-chloro- and 21-bromo-17α-acyloxy-20-keto-4-pregnenes involve multistep sequences of reactions. One method comprises converting the 17α,21-dihydroxy pregnene to the 21-sulfonate ester thereof followed by reaction with an inorganic chloride or bromide to yield the corresponding 21-chloro- or 21-bromo-17α-hydroxy-4-pregnene, and thence selective acylation of the 17α-hydroxyl group (during which step acylation of the 11β-hydroxyl group or aromatization of the A-ring may occur, unless the 11β-hydroxyl and/or the 3-keto functions are protected, which requires additional reaction steps) to give the 21-chloro or 21-bromo-17α-acyloxy-4-pregnene. In an alternative prior art method, a 17α,21-dihydroxy pregnene is converted to the corresponding 17α,21-cyclic orthoester, then selectively hydrolyzed to the 17α-ester, after which the 21-hydroxyl group is converted to the 21-chloro group via the 21-sulfonate, a step which requires forcing conditions (e.g. high temperatures) and which proceeds at a slow rate. Each of the foregoing routes involves a selective reaction which can be difficult and which involves three or four steps.

By the process of this invention, good yields of pure 21-halogeno-17α-acyloxy-20-ketopregnenes are easily prepared in one step from the 17α,21-orthoester by reaction with a triphenylmethyl halide without the necessity of protecting other functional groups (e.g. the 11β-hydroxyl or 3-ketone) present in the molecule and thence removing the protecting groups when the reaction is completed.

GENERAL DESCRIPTION OF THE INVENTION

The process of this invention, whereby a 17α,21-dihydroxy-20-ketopregnene 17α,21-orthoester is converted to a 21-halogeno-17α-acyloxy-20-ketopregnene, is defined as the process for the preparation of a 21-halogeno-17α-acyloxy-20-ketopregnene, said halogeno being chloro or bromo, which comprises reacting a 17α,21-dihydroxy-20-ketopregnene 17α,21-orthoester with triphenylmethyl halide, said halide being chloride or bromide, in an organic solvent.

The preferred mode of my process is that wherein said triphenylmethyl halide is triphenylmethyl chloride.

Of the 21-halogeno-17α-acyloxy-20-ketopregnenes prepared by the process of this invention, those specifically contemplated include 4-pregnenes of the following formula I and the 1-dehydro-, 6-dehydro- and 1,6-bis-dehydro analogs thereof:

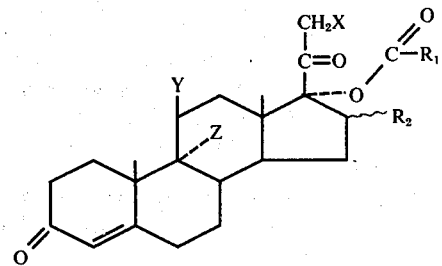

wherein
X is chlorine or bromine;
Y is hydrogen, oxo, hydroxy, lower alkanoyloxy, chlorine or fluorine;
Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;
$R_1$ is alkyl of 1 to 8 carbon atoms, or phenyl; and
$R_2$ is hydrogen, α-methyl, β-methyl, α-acyloxy of the formula

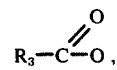

wherein $R_3$ is a lower alkyl having 1 to 8 carbon atoms.

The foregoing are known compounds possessing, in general, progestational, glucocorticoid and anti-inflammatory activities and, as such, can be used in the same manner as other know progestational and anti-inflammatory agents. The foregoing are particularly useful as topical anti-inflammatory agents, a preferred group of compounds prepared by my process being the 1-dehydro analogs of formula I, particularly those wherein X is chlorine, said compounds having high topical activity.

Both triphenylmethyl chloride and triphenylmethyl bromide reagents used in this process are known compounds which are commercially available.

My process is preferably carried out in an organic solvent in which both the steroid starting compound and the reagents are soluble and which will not react with the reagent so that competing side reactions are minimized. Suitable organic solvents for this process include 1,2-dimethoxyethane (glyme); bis (2-methoxyethyl)ether (diglyme); cyclic ethers such as dioxane and tetrahydrofuran; and preferably halogenated hydrocarbons such as carbon tetrachloride, chloroform, ethylenedichloride and, in particular, methylene chloride.

My process is usually carried out at the reflux temperature of the solvent, preferably methylene chloride, until the reaction is completed as determined by thin layer chromatography (usually from 2 to 22 hours). The reaction is advantageously run under anhydrous conditions and may be carried out under an inert atmosphere, e.g. under argon or nitrogen; however, this is not necessary.

The requisite starting compounds of my process are 17α,21-orthoesters of the 17α,21-dihydroxy analogs of the compounds defined by formula I. The orthoesters are obtained from the corresponding 17α,21-dihydroxy-20-ketopregnenes by known reaction with a trialkyl orthoester in a polar organic solvent, e.g. dimethylformamide or dimethylsulfoxide, in the presence of an acid catalyst, e.g. p-toluenesulfonic acid. The reaction may be carried out under an inert atmosphere, e.g. nitrogen or argon, although this is not necessary. The reaction is usually carried out at room temperature for a period of time ranging from 2 to 24 hours; however, when preparing a 17α,21-alkylorthobenzoate the reaction is preferably carried out in dioxane/benzene at reflux temperature.

The starting compounds of my process include 17α,21-dihydroxy-20-ketopregnene 17α,21-orthoesters having the following formula II:

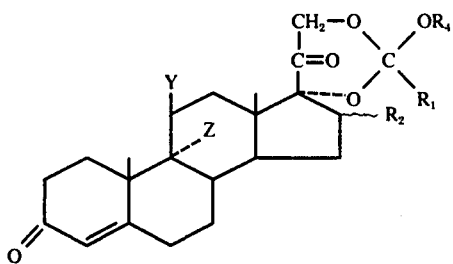

wherein

Y is hydrogen, oxo, hydroxy, lower alkanoyloxy, chlorine or fluorine;

Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;

$R_1$ is alkyl of 1 to 8 carbon atoms, or phenyl;

$R_2$ is hydrogen, α-methyl, β-methyl, α-acyloxy of the formula

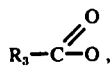

wherein $R_3$ is a lower alkyl having 1 to 8 carbon atoms;

$R_4$ is alkyl having 1 to 4 carbon atoms; and the 1-dehydro-, 6-dehydro- and 1,6-bis-dehydro analogs thereof.

Preferred starting compounds of my process are compounds of formula II wherein Y is hydroxy, chlorine or fluorine; Z is hydrogen, fluorine, chlorine or bromine when Y is hydroxy; and Z is chlorine when Y is chlorine or fluorine; and $R_1$ is alkyl of 1 to 8 carbon atoms. Particularly preferred are the 1-dehydro analogs of the foregoing.

Compounds of formula II are made by reaction of the corresponding 17α,21-dihydroxy steroid with a trialkyl orthoester of the formula

wherein $R_1$ is alkyl of 1 to 8 carbon atoms or phenyl and $R_4$ is an alkyl of from 1 to 4 carbon atoms.

In a preferred mode of carrying out my process, to one mole of a steroidal 17α,21-orthoester of formula II in a halogenated solvent (usually methylene chloride) there is added at least an equimolar amount (and usually about 5 moles per mole of steroid) of a triphenylmethyl halide, said halide being chloride or bromide. The reaction is heated at reflux temperature (optionally under an inert atmosphere) until the reaction is completed as determined by thin layer chromatography (usually 2 to 24 hours). The resulting 21-halogeno-17α-acyloxy-20-keto-4-pregnene is then isolated utilizing conventional techniques, usually via chromatographic techniques.

The following examples illustrate specific embodiments of the invention.

PREPARATION OF INTERMEDIATES

PREPARATION 1

9α,11β-Dichloro-16α-Methyl-1,4-Pregnadiene-17α,21-Diol-',20-Dione 17,21-methylorthobenzoate and the 1,2-Dihydro Analog thereof A. To a solution of 2 gms. of 9α,11β-dichloro-16α-methyl-1,4-pregnadiene-17α,21-diol-3,20-dione in 112 ml. of dioxane and 168 ml. of benzene add 2 ml. of trimethylorthobenzoate and 200 mg. of pyridinium p-toluenesulfonate and heat at reflux temperature for 24 hours. Add an additional 2 ml. portion of trimethylorthobenzoate and 200 mg. of pyridinium p-toluenesulfonate and heat at reflux temperature for 3 more days. Distill off about ⅓ of the solvent, add about 6 drops of pyridine and then distill the remaining solvent in vacuo at room temperature. Triturate the resulting residue with petroleum ether and decant the petroleum ether wash to obtain a residue comprising 9α,11β-dichloro-16α-methyl-1,4-pregnadiene-17α,21-diol-3,20-dione 17,21-methylorthobenzoate, which is used without further purification in the process of this application.

B. In a manner similar to that described in above Preparation 1A, treat 9α,11β-dichloro-16α-methyl-4-pregnene-17α,21-diol-3,20-dione in dioxane and benzene with trimethylorthobenzoate and pyridinium p-toluenesulfonate; evaporate the solvents, then wash the resultant product with petroleum ether in a manner similar to that described to obtain 9α,11β-dichloro-16α-methyl-4-pregnene-17,21-diol-3,20-dione 17,21-methylorthobenzoate.

PREPARATION 2

1,4-Pregnadiene-11β,17α,21-Triol-3,20-Dione 17,21-n-Butyl-orthopropionate and the 1,2-Dihydro Analog Thereof A. To a solution of 2 gms. of 1,4-pregnadiene-11β,17α,21-triol-3,20-dione in 10 ml. of dimethylsulfoxide add 150 mg. of p-toluenesulfonic acid and 3.6 ml. of tri-n-butylorthopropionate. Stir the reaction mixture at room temperature for 3.5 hours, then pour onto 600 ml. of ice water to which has been added 300 ml. of saturated sodium bicarbonate solution. Separate the resultant precipitate by filtration and wash the precipitate with copious amounts of water. Dissolve the precipitate in ethyl acetate. Dry the ethyl acetate solution over anhydrous magnesium sulfate and evaporate in vacuo to a residue comprising 1,4-pregnadiene-11β,17α,21-triol-3,20-dione 17,21-n-butylorthopropionate.

B. In similar manner, treat 4-pregnene-11β,17α,21-triol-3,20-dione in dimethylsulfoxide with p-toluenesulfonic acid and tri-n-butylorthopropionate to obtain 4-pregnene-11β,17α,21-triol-3,20-dione 17,21-n-butylorthopropionate.

PREPARATION 3

9α,11β-Dichloro-16α-Methyl-1,4-Pregnadiene-17α,21-Diol-3,20-Dione 17,21-n-butylorthopropionate and the 1,2-Dihydro Analog Thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 3.6 ml. of tri-n-butylorthopropionate. Stir the reaction mixture at room temperature for 4 hours, then pour onto 600 ml. of ice water, to which has been added 300 ml. of saturated sodium bicarbonate solution. Separate the resultant precipitate by filtration and wash the precipitate with copious amounts of water. Dissolve the precipitate in ethyl acetate, dry the ethyl acetate over anhydrous magnesium sulfate and evaporate in vacuo to a residue comprising 9α,11β-dichloro-16α-methyl-1,4-pregnadiene-17α,21-diol-3,20-dione 17,21-n-butylorthopropionate.

B. In similar manner, treat 9α,11β-dichloro-16α-methyl-4-pregnene-17α,21-diol-3,20-dione in dimethylsulfoxide with p-toluenesulfonic acid and tri-n-butylorthopropionate to obtain 9α,11β-dichloro-4-pregnene-17α,21-diol-3,20-dione 17,21-n-butylorthopropionate.

PREPARATION 4

9α,11β-Dichloro-16α-Methyl-1,4-Pregnadiene-17α,21-Diol-3,20-Dione 17,21-n-butylorthovalerate and the 1,2-Dihydro Analog Thereof A. To a solution of 2 gm. of 9α,11β-dichloro-16α-methyl-1,4-pregnadiene-17α,21-diol-3,20-dione in 12 ml. of dimethylsulfoxide add 150 mg. of p-toluenesulfonic acid and 4 ml. of tri-n-butylorthovalerate. Stir at room temperature for 4 hours, then add 600 ml. of ice water, to which has been added 300 ml. of saturated sodium bicarbonate. Isolate the resultant product in a manner similar to that described in Preparation 3A to obtain 9α,11β-dichloro-16α-methyl-1,4-pregnadiene-17α,21-diol-3,20-dione 17,21-n-butylorthovalerate.

B. Treat a solution of 9α,11β-dichloro-16α-methyl-4-pregnene 17α,21-diol-3,20-dione in dimethylsulfoxide with p-toluenesulfonic acid and tri-n-butylorthovalerate in a manner similar to that described hereinabove to obtain 9α,11β-dichloro-16α-methyl-4-pregnene-17α,21-diol-3,20-dione-3,20-dione 17,21-n-butylorthovalerate.

PREPARATION 5

9α-Fluoro-16β-Methyl-1,4-Pregnadiene-11β,17α,21-Triol-3,20-Dione 17,21-n-Butylorthopropionate and the 1,2-Dihydro Analog Thereof A. In a manner similar to that described in Preparation 2A, treat 3 gm. of 9α-fluoro-16β-methyl-1,4-pregnadiene-11β,17α,21-triol-3,20-dione in 9 ml. of dimethylsulfoxide with 225 mg. of p-toluenesulfonic acid and 5.4 ml. of tri-n-butylorthopropionate at room temperature for 4 hours. Isolate and purify the resultant product in a manner similar to that described to obtain 9α-fluoro-16β-methyl-1,4-pregnadiene-11β,17α,21-triol-3,20-dione 17,21-n-butylorthopropionate.

B. In a manner similar to that described hereinabove, treat 9α-fluoro-16β-methyl-4-pregnene-11β,17α,21-triol-3,20-dione in dimethylsulfoxide with p-toluenesulfonic acid and tri-n-butylorthopropionate to obtain 9α-fluoro-16β-methyl-4-pregnene-11β,17α,21 triol-3,20-dione 17,21-n-butylorthopropionate.

PREPARATION 6

16α-Methyl-1,4-Pregnadiene-11β,17α,21-Triol-3,20-Dione 17,21-n-Butylorthopropionate and the 1,2-Dihydro Analog Thereof A. To a solution of 0.75 gm. of 16α-methyl-1,4-pregnadiene-11β,17α,21-triol-3,20-dione in 3.75 ml. of dimethylsulfoxide add 56.5 mg. of p-toluenesulfonic monohydrate and 2.25 ml. of tri-n-butylorthopropionate and stir and the reaction mixture at room temperature for 3 hours. Pour into a mixture of 400 ml. of ice water and 100 ml. of saturated sodium bicarbonate solution. Decant the aqueous layer and triturate the gummy residue with hexane. Separate the resultant precipitate by filtration and dry at room temperature in vacuo to obtain 16α-methyl-1,4-pregnadiene-11β,17α,21-triol-3,20-dione 17,21-n-butylorthopropionate (yield 0.87 gm).

B. In a manner similar to that described hereinabove, treat 16α-methyl-4-pregnene-11β,17α,21-triol-3,20-dione in dimethylsulfoxide with p-toluenesulfonic monohydrate in tri-n-butylorthopropionate and isolate the resultant product is the described manner to obtain 16α-methyl-4-pregnene-11β,17α,21-triol-3,20-dione 17,21-n-butylorthopropionate.

PREPARATION 7

9α-Fluoro-16α-Methyl-1,4-Pregnadiene-11β,17α,21-Triol-3,20-Dione 17,21-Methylorthobenzoate and the 1,2-Dihydro Analog Thereof A. To 1 gm. of 9α-fluoro-16α-methyl-1,4-pregnadiene-11β,17α,21-triol-3,20-dione in 64 ml. of dioxane and 84 ml. of benzene add 1 ml. of trimethylorthobenzoate and 100 mg. of pyridinium p-toluenesulfonate. Heat the reaction mixture at reflux temperature for 3 days, then distill ⅓ of the solvent at atmospheric pressure, add 5 drops of pyridine, then distill the remaining solvent in vacuo at room temperature. Triturate the resultant residue with petroleum ether and filter the resultant solid comprising 9α-fluoro-16α-methyl-1,4-pregnadiene-11β,17α,21-triol-3,20-dione 17,21-methylorthobenzoate.

B. Treat 9α-fluoro-16α-methyl-4-pregnene-11β,17α,21-triol-3,20-dione in dioxane and benzene with trimethylorthobenzoate and pyridinium p-toluenesulfonate in the manner described hereinabove to obtain 9α-fluoro-16α-methyl-4-pregnene-11β,17α,21-triol-3,20-dione 17,21-methylorthobenzoate.

PREPARATION 8

9α-Fluoro-16α-Methyl-1,4-Pregnadiene-11β,17α,21-Triol-3,20-Dione 17,21-n-Butylorothopropionate and the 1,2-Dihydro Analog Thereof A. In a manner similar to that described in Preparation 6A, treat 9α-fluoro-16α-methyl-1,4-pregnadiene-11β,17α,21-triol-3,20-dione in dimethylsulfoxide with p-toluenesulfonic monohydrate and tri-n-butylorthopropionate. Isolate and purify the 9α-fluoro-16α-methyl-1,4-pregnadiene-11β,17α,21-triol-3,20-dione 17,21-n-butylorthopropionate.

B. In a manner similar to that described hereinabove, treat 9α-fluoro-16α-methyl-4-pregnene-11β,17α,21-triol-3,20-dione in dimethylsulfoxide with p-toluenesulfonic monohydrate and tri-n-butylorthopropionate to obtain 9α-fluoro-16α-methyl-4-pregnene11β, 17α,21-triol-3,20-dione 17,21-n-butylorthopropionate.

PREPARATION 9

1,4,6-Pregnatriene-11β,17α,21-Triol-3,20-Dione 17,21-n-Butylorthopropionate and the 1,2-Dihydro Analog Thereof A. To a solution of 60 mg. of 1,4,6-pregnatriene-11β,17α,21 triol-3,20-dione in 0.5 ml. of dimethylsulfoxide add 5 mg. of p-toluenesulfonic acid and 0.3 ml. of tri-n-butylorthopropionate. Stir at room temperature for 3 hours, pour into saturated sodium bicarbonate solution and extract with ethyl acetate. Dry the combined ethyl acetate extracts over magnesium sulfate, then evaporate in vacuo to a residue comprising 1,4,6-pregnatriene-11β,17α,21-triol-3,20-dione 17,21-n-butylorthopropionate.

B. In a manner similar to that described hereinabove, treat 4,6-pregnadiene-11β,17α,21-triol-3,20-dione in dimethylsulfoxide with p-toluenesulfonic acid and tri-n-butylorthopropionate to obtain 4,6-pregnadiene-11β,17α,21-triol-3,20-dione 17,21-n-butylorthopropionate.

PREPARATION 10

9α-Fluoro-16β-Methyl-17α,21-Diol-3,11,20-Trione 17,21-methylortho-n-butyrate and the 1,2-Dihydro Analog Thereof A. In a manner similar to that described in Preparation 4A, treat 9α-fluoro-16β-methyl-1,4pregnadiene-11β,17α-diol-3,11,20-trione in dimethylsulfoxide with p-toluenesulfonic acid and trimethylortho-n-butyrate. Isolate and purify the resultant product in a manner similar to that described to obtain 9α-fluoro-16β-methyl11β,17α-diol-3,11,20-trione 17,21-methylorthobutyrate.

B. In a manner similar to that described hereinabove, treat 9α-fluoro-16β-methyl-4-pregnene-17α,21-diol-3,11,20-trione in dimethylsulfoxide with p-toluenesulfonic acid and trimethylortho-n-butyrate to obtain 9α-fluoro-16β-methyl-4-pregnene-17α,21-diol-3,11,20-trione 17,21-methylortho-n-butyrate.

PREPARATION 11

6α,9α-Difluoro-16β-Methyl-1,4-Pregnadiene-11β,17α21-Triol-3,20-Dione 17,21-Ethylorthoacetate and the 1,2-Dihydro Analog Thereof A. In a manner similar to that described in Preparation 5A, treat 6α,9α-difluoro-16β-methyl-1,4-pregnadiene-11β,17α,21-triol-3,20-dione in dimethylsulfoxide with p-toluenesulfonic acid and triethylorthoacetate. Isolate and purify the resultant product in a manner similar to that described to obtain 6α,9α-difluoro-16β-methyl-1,4-pregnadiene-11β,17α,21-triol-3,20-dione 17,21-ethylorthoacetate.

B. In a manner similar to that described hereinabove, treat 6α,9α-difluoro-16β-methyl-4-pregnene-11β,17α,21-triol-3,20-dione in dimethylsulfoxide with p-toluenesulfonic acid and triethylorthoacetate to obtain 6α,9α-difluoro-16β-methyl-4-pregnene-11β,17α,21-triol-3,20-dione 17,21-ethylorthoacetate.

EXAMPLE 1

21-BROMO-1,4-PREGNADIENE-11β,17α-DIOL-3,20-DIONE 17-PROPIONATE AND THE 1,2-DIHYDRO ANALOG THEREOF PREPARED UTILIZING TRITYL BROMIDE AS REAGENT

A. To a solution of 0.55 gm. of 1,4-pregnadiene-11β,17α,21-triol-3,20-dione 17,21-n-butylorthopropionate in 55 ml. of methylene chloride add 1.89 gm. (5 equivalents) of trityl bromide. Heat the reaction mixture at reflux temperature for 20 hours, then evaporate in vacuo and chromatograph the resultant residue on 100 gm. of silica gel eluting with chloroform: ethyl acetate (3:1). Combine the like eluates as determined by thin layer chromatography and evaporate the combined eluates to a residue comprising 21-bromo-1,4-pregnadiene-11β,17α-diol3,20-dione 17-propionate (yield 164 mg., 30% theory); m.p. 216°–218° C; $[\alpha]_D^{26}$ + 84.5 (dimethylformamide); nmr (dmso-d₆); δ 0.88 ($C_{13}$-$CH_3$); 1.4 ($C_{10}$-$CH_3$); 1.4 ($C_{10}$-$CH_3$); 4.24 ($C_{21}$-$CH_2$; s).

B, Treat 4-pregnene-11β,17α,21-triol-3,20-dione 17,21-n-butylorthopropionate in methylene chloride with trityl bromide in a manner similar to that described in Example 1A. Isolate and purify the resultant product in a manner similar to that described to obtain 21-bromo-4-pregnene-11β,17α-diol-3,20-dione 17-propionate.

C. In the procedures of Examples 1A and 1B, substitute trityl chloride for trityl bromide to obtain, respectively, 21-chloro1,4-pregnadiene-11β,17α-diol-3,20-dione 17-propionate and 21-chloro-4-pregnene-11β,17α-diol-3,20-dione 17-propionate.

EXAMPLE 2

9α-FLUORO-21-CHLORO-16α-METHYL-1,4-PREGNADIENE-11β,17α-DIOL-3,20-DIONE 17-PROPIONATE AND THE 1,2-DIHYDRO ANALOG THEREOF

A. To a solution of 1.3 gm. of 9α-fluoro-16α-methyl-1,4-pregnadiene-11β,17α,21triol-3,20-dione 17,21-n-butylorthopropionate in 65 ml. of methylene chloride add 3.59 gm. (5 molar equivalents) of trityl chloride. Heat the reaction mixture at reflux temperature for 22 hours under anhydrous conditions. Evaporate the reaction mixture to a residue, add 50% aqueous acetic acid to the residue and stir for 10 minutes, extract the acetic acid mixture with methylene chloride and evaporate the combined methylene chloride extracts in vacuo to a residue. Chromatograph the residue on a column of silica gel eluting with chloroform:ethyl acetate (3:1). Combine the like eluates as determined by thin layer chromatography and evaporate the combined eluates in vacuo to a residue comprising 9α-fluoro-21-chloro-16α-methyl-1,4-pregnadiene-11β,17α-diol-3,20-dione 17-propionate (yield 0.26 gm., 22% theory).

B. Carry out the procedures described in Example 2A starting with 9α-fluoro-16α-methyl-4-pregnene-11β,17α,21-triol-3,20-dione 17,21-n-butylorthopropionate to obtain 9α-fluoro-21-chloro-16α-methyl-4-pregnene-11β,17α-diol-3,20-dione 17-propionate.

C. In Examples 2A and 2B, by utilizing trityl bromide instead of trityl chloride, there is obtained the corresponding 21-bromo-4-pregnene derivative, i.e. 9α-fluoro-21-bromo-16α-methyl-1,4-pregnadiene-11β,17α-diol-3,20-dione 17-propionate and 9α-fluoro- 21-bromo-16α-methyl-4-pregnene-11β,17α-diol-3,20-dione 17-propionate, respectively.

EXAMPLE 3

PREPARATION OF OTHER 21-CHLORO AND 21-BROMO-17α-ACYLOXY-20KETO-1,4-PREGNADIENES AND THE 1,2-DIHYDRO ANALOGS THEREOF

A. In a manner similar to that described in Example 2 treat each of the folliwing 17,21-dihydroxy-20-keto-1,4-pregnadiene-17,21-orthoesters with triphenylmethyl chloride in methylene chloride at reflux temperature:

9α,11β-dichloro-16α-methyl-1,4-pregnadiene-17α,21-diol-3,20-dione 17,21-methylorthobenzoate and the 1,2-dihydro analog thereof;

9α,11β-dichloro-16α-methyl-1,4-pregnadiene-17α,21-diol-3,20-dione 17,21-n-butylorthopropionate and the 1,2-dihydro analog thereof;

9α11β-dichloro-16α-methyl-1,4-pregnadiene-17α,21-n-butylorthovalerate and the 1,2-dihydro analog thereof;

9α-fluoro-16β-methyl-1,4-pregnadiene-11β,17α,21-triol-3,20-dione 17,21-n-butylorpropionate and the 1,2-dihydro analog thereof;

16α-methyl-1,4-pregnadiene-11β,17α,21-triol-3,20-dione-17,21-n-butylorthopropionate and the 1,2-dihydro analog thereof;

9α-fluoro-16α-methyl-1,4-pregnadiene-11β,17α,21-triol-3,20-dione 17,21-n-butylorthopropionate and the 1,2-dihydro analog thereof;

1,4,6-pregnatriene-11β,17α,21-triol-3,20-dione 17,21-n-butylorthopropionate and the 1,2-dihydro analog thereof;

9α-fluoro-16β-methyl-1,4-pregnadiene-17α,21-diol-3,11,20-trione 17,21-methylortho-n-butyrate and the 1,2-dihydro analog thereof; and 6α,9α-difluoro-16β-methyl-1,4-pregnadiene-11β,17α,21-triol-3,20-dione 17,21-ethylorthoacetate and the 1,2-dihydro analog thereof.

Isolate and purify each of the resultant products in a manner similar to that described in Example 2 to obtain, respectively:

9α,11β,21-trichloro-16α-methyl-1,4-pregnadiene-17α-ol-3,20-dione 17-benzoate;

9α,11β,21-trichloro-16α-methyl-4-pregnene-17α-ol-3,20-dione 17-benzoate;

9α,11β-21-trichloro-16α-methyl-1,4-pregnadiene-17α-ol-3,20-dione 17-propionate;

9α,11β,21-trichloro-16α-methyl-4pregnene-17α-ol-3,20-dione 17-propionate;

9α,11β,21-trichloro-16α-methyl-1,4-pregnadiene-17α-ol-3,20-dione 17-valerate;

9α,11β,21-trichloro-16α-methyl-4-pregnene-17α-ol-3,20-dione 17-valerate;

9α-fluoro-21-chloro-16β-methyl-1,4-pregnadiene-11β,17α-diol-3,20-dione 17-propionate;

9α-fluoro-21-chloro-16β-methyl-4-pregnene-11β,17α-diol-3,20-dione 17-propionate;

16α-methyl-21-chloro-1,4-pregnadiene-11β,17α-diol-3,20-dione 17-propionate;

16α-methyl-21-chloro-4-pregnene-11β,17α-diol-3,20-dione 17-propionate;

9α-fluoro-21-chloro-16α-methyl-1,4-pregnadiene-11β,17α-diol-3,20-dione 17-propionate;

9α-fluoro-21-chloro-16α-methyl-1,4-pregnadiene-11β,17α-diol-3,20-dione 17-propionate;

9α-fluoro-21-chloro-16α-methyl-4-pregnene-11β,17α-diol-3,20-dione 17-propionate;

21-chloro-1,4,6-pregnatriene-11β,17α-diol-3,20-dione 17-propionate;

21-chloro-4,6-pregnadiene-11β,17α-diol-3,20-dione 17-propionate;

9α-fluoro-21-chloro-16β-methyl-1,4-pregnadiene-17α-ol-3,11,20-trione 17-n-butyrate; 9α-fluoro-21-chloro-16β-methyl-4-pregnene-17α-ol-3,11,20-trione 17-n-butyrate;

6α,9α-difluoro-21-chloro-16β-methyl-1,4-pregnadiene-11β,17α-diol-3,20-dione-3,20-dione 17-acetate;

6α,9α-difluoro-21-chloro-16β-methyl-4-pregnene-11β,17α-diol-3,20-dione 17-acetate.

B. In a manner similar to that described in Example 1 treat each of the 17α,21-dihydroxy-20-keto-4-pregnene 17,21-orthoester starting compounds of above Example 3A with trimethylphenyl bromide. Isolate and purify each of the resultant products in a manner similar to that described in Example 1 to obtain, respectively:

9α,11β-dichloro-21-bromo-16α-methyl-1,4-pregnadiene-17α-ol-3,20-dione 17-benzoate;

9α,11β-dichloro-21-bromo-16α-methyl-4-pregnene-17α-ol-3,20-dione 17-benzoate;

9α,11β-dichloro-21-bromo-16α-methyl-1,4-pregnadiene-17α-ol-3,20-dione 17-propionate;

9α,11β-dichloro-16α-methyl-17α-ol-3,20-dione 17-propionate;

9α,11β-dichloro-21-bromo-16α-methyl-1,4-pregnadiene-17α-ol-3,20-dione 17-valerate;

9α,11β-dichloro-21-bromo-16α-methyl-4-pregnene-17α-ol-3,20-dione 17-valerate;

9α-fluoro-21-bromo-16β-methyl-1,4-pregnadiene-11β,17α-diol-3,20-dione 17-propionate;

9α-fluoro-21-bromo-16β-methyl-4-pregnene-11β,17α-diol-3,20-dione 17-propionate;

21-bromo-16α-methyl-1,4-pregnadiene-11β,17α-diol-3,20-dione 17-propionate;

21-bromo-16α-methyl-4-pregnene-11β,17α-diol-3,20-dione 17-propionate;

9α-fluoro-21-bromo-16α-methyl-1,4-pregnadiene-11β,17α-diol-3,20-dione 17-propionate;

9α-fluoro-21-bromo-16α-methyl-4-pregnene-11β,17α-diol-3,20-dione 17-propionate;

21-bromo-1,4,6-pregnatriene-11β,17α-diol-3,20-dione 17-propionate;

21-bromo-4,6-pregnadiene-11β,17α-diol-3,20-dione 17-propionate;

9α-fluoro-21-bromo-16β-methyl-1,4-pregnadiene-17α-ol-3,11,20-trione 17-n-butyrate;

9α-fluoro-21-bromo-16β-methyl-4-pregnene-17α-ol-3,11,20-trione 17-n-butyrate;

6α,9α-dichloro-21-bromo-16β-methyl-1,4-pregnadiene11,62 ,17α-diol-3,20-dione 17-acetate;

6α,9α-difluoro-21-bromo-16β-methyl-4-pregnene-11β,17α-diol-3,20-dione 17-acetate.

I claim:

1. The process for the preparation of a 21-halogeno-17α-acyloxy-20-ketopregnene, said halogeno being chloro or bromo, which comprises the reaction of a 17,21-dihydroxy-20-ketopregnene 17,21-orthoester with a triphenylmethyl halide, said halide being chloride or bromide, in an organic solvent.

2. The process of claim 1 wherein said halide reagent is triphenylmethyl bromide.

3. The process of claim 1 wherein said 17,21-dihydroxy-20-ketopregnene 17,21-orthoester is a member selected from the group consisting of a compound defined by formula I:

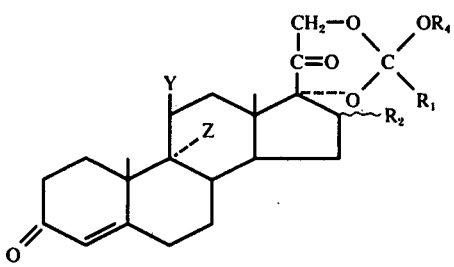

wherein
Y is hydrogen, oxo, hydroxy, lower alkanoyloxy, chlorine or fluorine;
Z is hydrogen, fluorine, chlorine or bromine when Y is oxo, hydroxy or lower alkanoyloxy; Z is chlorine or bromine when Y is chlorine or fluorine; and Z is hydrogen when Y is hydrogen;
$R_1$ is alkyl of 1 to 8 carbon atoms, or phenyl;
$R_2$ is hydrogen, α-methyl, β-methyl, α-acyloxy of the formula

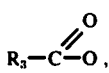

wherein $R_3$ is a lower alkyl having 1 to 8 carbon atoms;
$R_4$ is alkyl having 1 to 4 carbon atoms;
and the 1-dehydro-, 6-dehydro- and 1,6-bis-dehydro analogs of the compounds of formula I;
and wherein said organic solvent is a halogenated hydrocarbon at the reflux temperature of said solvent.

4. The process of claim 3 wherein the 17α,21-dihydroxy-20-ketopregnene 17,21-orthoester is a compound of the formula:

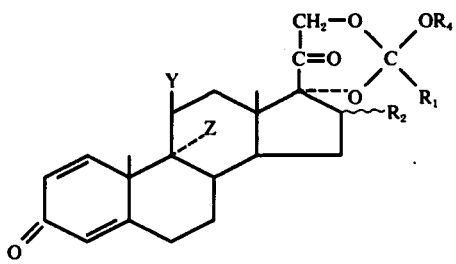

5. The process of claim 4 wherein the halide reagent is triphenylmethyl chloride.

6. A process for preparing a 21-chloro-17-acyloxy-20-ketopregnene from a 17,21-dihydroxy-20-ketopregnene, cyclic 17,21-orthoester which comprises reacting a 17,21-dihydroxy-20-ketopregnene, cyclic 17,21-orthoester with triphenylmethyl chloride in an organic solvent at the reflux temperature of the solvent.

7. The process of claim 6 wherein the 17,21-dihydroxy-20-ketopregnene, cyclic 17,21-orthoester has the formula:

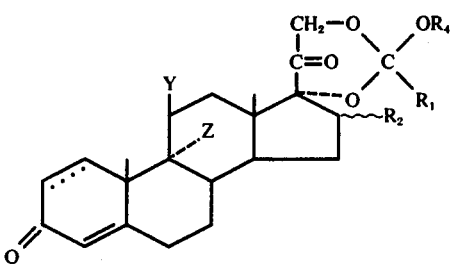

wherein
Y is hydroxy, chlorine or fluorine;
Z is hydrogen, fluorine, chlorine, or bromine when Y is hydroxy, and Z is chlorine when Y is chlorine or fluorine;
$R_1$ is alkyl of 1 to 8 carbon atoms;
$R_2$ is hydrogen, α-methyl, β-methyl, α-acyloxy of the formula

wherein $R_3$ is a lower alkyl having 1 to 8 carbon atoms; and
$R_4$ is alkyl of 1 to 4 carbon atoms.

8. A process in accordance with claim 7 wherein the 17α,21-dihydroxy-20-ketopregnene, cyclic 17,21-orthoester has the formula

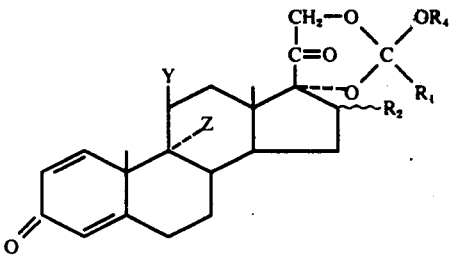

9. A process in accordance with claim 6 wherein the organic solvent is a halogenated hydrocarbon.

* * * * *

UNITED STATES PATENT OFFICE
CERTIFICATE OF CORRECTION

Patent No. 4,021,459   Dated May 3, 1977

Inventor(s) Michael J. Green

It is certified that error appears in the above-identified patent and that said Letters Patent are hereby corrected as shown below:

Column 4, line 12, "-17$\alpha$,21-Diol-',20-Dione-" should read ---17$\alpha$,21-Diol-3,20-Dione---; line 23, "about 1/3 of" should read ---about 2/3 of---. Column 6, line 39, "distill 1/3 of" should read ---distill 2/3 of---. Column 8, line 21, "1.4 ($C_{10}$-$CH_3$); 1.4 ($C_{10}$-$CH_3$);" should read ---1.4 ($C_{10}$-$CH_3$);--- Column 9, lines 21 and 22, "-17$\alpha$,21-n-butylorthovalerate-" should read ---17$\alpha$,21-diol-3,20-dione 17,21-n-butylorthovalerate---; lines 65-68, "-9$\alpha$-fluoro-21-chloro-16$\alpha$-methyl-1,4-pregnadiene-11$\beta$,17$\alpha$-diol-3,20-dione 17-propionate; 9$\alpha$-fluoro-21-chloro-16$\alpha$-methyl-1,4-pregnadiene-11$\beta$,17$\alpha$-diol-3,20-dione 17-propionate;" should read ---9$\alpha$-fluoro-21-chloro-16$\alpha$-methyl-1,4-pregnadiene-11$\beta$,17$\alpha$-diol-3,20-dione 17-propionate;---. Column 10, line 12, "-3,20-dione-3,20-dione-" should read ---3,20-dione---; line 55, "-11,62,17$\alpha$-diol-" should read -11$\beta$,17$\alpha$-diol---.

Signed and Sealed this second Day of August 1977

[SEAL]

Attest:

RUTH C. MASON
Attesting Officer

C. MARSHALL DANN
Commissioner of Patents and Trademarks